US00PP08449P

United States Patent [19]

Meilland

[11] Patent Number: Plant 8,449

[45] Date of Patent: Nov. 9, 1993

[54] FLORIBUNDA ROSE PLANT NAMED 'MEIBALTAZ'

[75] Inventor: Alain A. Meilland, Antibes, France

[73] Assignee: The Conard-Pyle Company, West Grove, Pa.

[21] Appl. No.: 971,603

[22] Filed: Oct. 30, 1992

[51] Int. Cl.[5] ..... A01H 5/00
[52] U.S. Cl. ..... Plt./24
[58] Field of Search ..... Plt./24, 15, 8.2

*Primary Examiner*—Howard J. Locker

*Attorney, Agent, or Firm*—Burns, Doane, Swecker & Mathis

[57] ABSTRACT

A new and distinct variety of Floribunda rose plant is provided which abundantly forms attractive long-lasting double aureolin yellow blossoms wherein the coloration is very stable upon the passage of time. The plant exhibits vigorous vegetation and a uniform compact growth habit. Very quick reflowering cycles are provided. The new variety is well adapted for growing as attractive ornamentation in parks and gardens. Very good resistance to cryptogamic diseases also is observed.

1 Drawing Sheet

SUMMARY OF THE INVENTION

The new variety of Floribunda rose plant was created by artificial pollination wherein two parents were crossed which previously had been studied in the hope that they would contribute the desired characteristics. The female parent (i.e., the seed parent) of the new variety was the product of the pollination of the Landora variety (non-patented in the United States) by the Meilenangal variety (non-patented in the United States). The male parent (i.e., the pollen parent) of the new variety was the Speck's Yellow variety (non-patented in the United States). The parentage of the new variety can be summarized as follows:

(Landora × Meilenangal) × Speck's Yellow.

The seeds resulting from the above pollination were sown and 12 small plants were obtained which were physically and biologically different from each other. Selective study resulted in the identification of a single plant of the new variety.

It was found that the new variety of Floribunda rose plant of the present invention possesses the following combination of characteristics:

(a) forms in abundance attractive long-lasting double blossoms which are of a very stable aureolin yellow coloration,
(b) forms medium green adult wood,
(c) exhibits a compact and uniform low growth habit,
(d) exhibits a very rapid reflowering cycles, and
(e) exhibits excellent resistance to diseases.

The new variety is particularly well suited for growing as attractive ornamentation in parks and gardens.

The new variety undergoes asexual propagation by a number of routes, including budding, grafting, cuttage, etc. The characteristics of the new variety have been fould to be strictly transmissible by such asexual propagation from one generation to another in France.

The new variety has been named the Meibaltaz variety.

BRIEF DESCRIPTION OF PHOTOGRAPH

The accompanying photograph shows as nearly true as it is reasonably possible to make the same, in a color illustration of this character, typical specimens of the plant parts of the new variety. The rose plants of the new variety were three years of age and were observed during September while budded on *Rosa froebelli* understock and growing outdoors at LeCannet des Maures, Var, France.

DETAILED DESCRIPTION

Figures 1, 2, 3, 4, 5, 6, 7, 8, 9, 10, 11, 12, 13, 14, 15, 16:
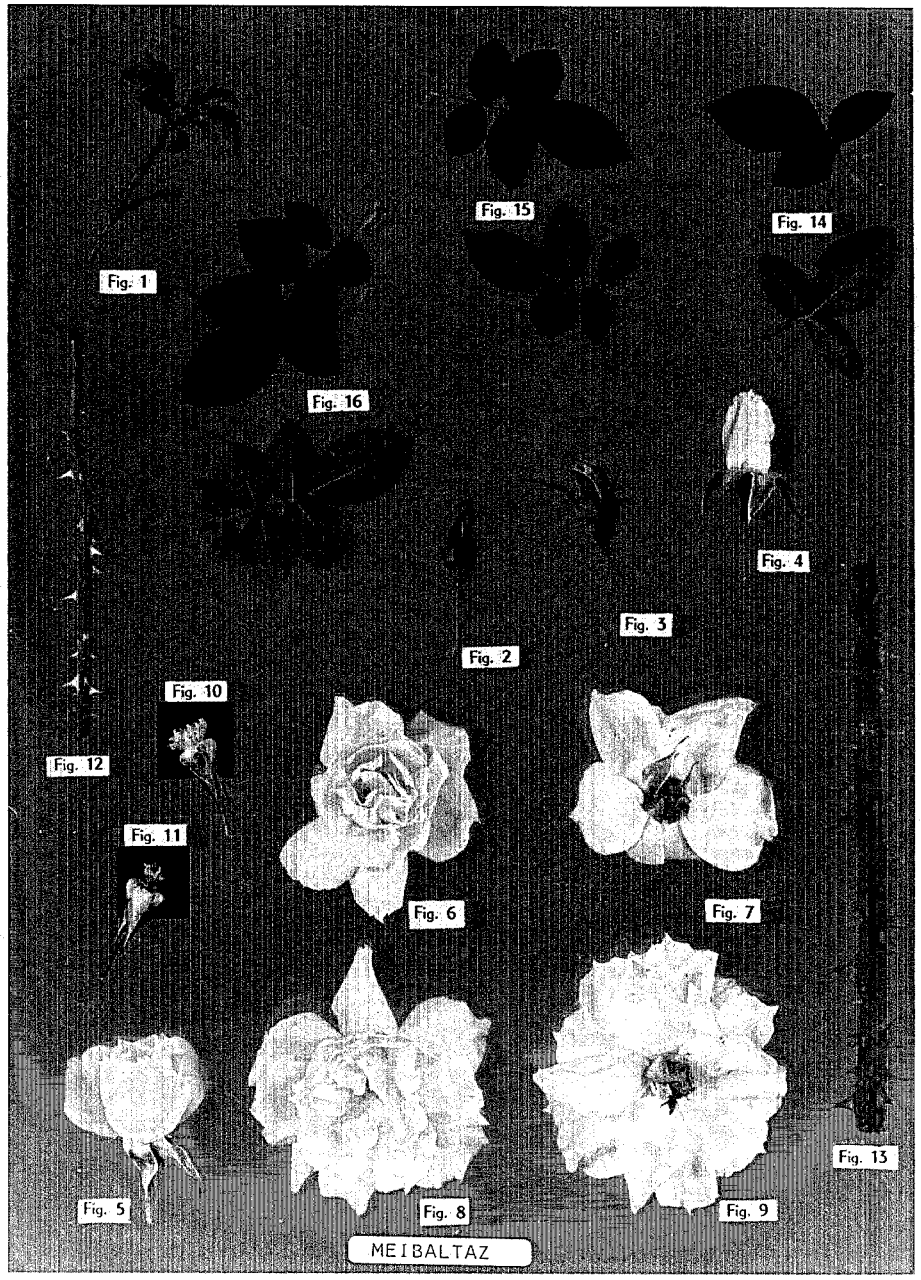
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower during the course of opening.
FIG. 6 illustrates a specimen of an open flower — plan view — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of an adult main branch.
FIG. 14 illustrates specimen of a pair of leaves with three leaflets — upper surface (top), and — under surface (bottom)
FIG. 15 illustrates a specimen of a pair of leaves with five leaflets — upper surface (top); and — under surface (bottom)
FIG. 16 illustrates a specimen of a pair of leaves with seven leaflets — upper surfce (top), and — under surface (bottom).

The chart used in the identification of the colors is that of The Royal Horticultural Society (R.H.S. Colour Chart). The terminology which precedes references to the chart has been added to indicate the corresponding color in more common terms. The description is based on three year old specimens of the new variety during September while budded on *Rosa froebelli* understock and growing outdoors at LeCannet des Maures, Var, France.

Class: Floribunda.

Plant:

*Height.*—Approximately 70 to 90 cm. at the end of the growing season (eighteen months after budding).

Habit.—Bushy.

Branches:

*Color.*—Young stems: light green, Green Group 138B. Adult wood: medium green, Yellow-Green Group 146C.

Thorns.—Size: large. Quantity: numerous. Color: greenish on young stems, and greenish changing to light tan on mature wood.

Leaves:

*Stipules.*—Adnate, pectinate, wide and linear.

*Petioles.*—Upper surface: striped reddish brown on young foliage and medium green on mature foliage with more or less glandular edges. Under surface: medium green, with a few prickles.

*Leaflets.*—Number: 3, 5, and 7. Shape: usually oval. Serration: single and regular. Texture: leathery. General appearance: dense and semi-matte foliage. Color (young foliage): Upper surface: medium green, Yellow-Green Group 146B. Under surface: light green, Yellow-Green Group 146D, and more or less suffused with reddish coloration. Color (adult foliage): Upper surface: bronze green, Yellow-Green Group 146A. Under surface: light green, Yellow-Green Group 146B.

Inflorescence:

*Number of flowers.*—Commonly 1 to 6 blooms per stem.

*Peduncle.*—Light green with more or less glandular edges, and approximately 5 cm. in length on average.

*Sepals.*—Upper surface: tomentose and greenish in coloration. Under surface: medium green, and the outer sepals commonly exhibit edges which are not appendiculated.

*Buds.*—Shape: egg-shaped. Length: approximately 3 to 3.5 cm. on average. Size: medium. Color upon opening: Upper surface: lemon yellow, Yellow Group 13A. Under surface: medium lemon yellow, Yellow Group 13B.

*Flower.*—Shape: cup-like, semi-double. Diameter: approximately 9 cm. on average. Color (when opening begins): Upper surface: aureolin, Yellow Group 12A. Under surface: medium aureolin, Yellow Group 12B. Color (when blooming): Upper surface: Aureolin, Yellow Group 12A. Under surface: light aureolin, Yellow Group 12C. Color (at end of opening): Upper surface: medium aureolin, Yellow Group 12B. Under surface: light aureolin, Yellow Group 12C. Fragrance: none. Lasting quality: very long lasting blooms. Petal drop: good. Petal number: approximately 27 to 30 on average. Petal texture: consistent. Petal shape: rounded with pointed tips. Stamen number: approximately 90 to 96 on average. Anthers: normal strong yellow in coloration. Filaments: normal yellow coloration, and are of irregular heights. Pistils: approximately 53 to 57 on average. Stigmas: greenish in coloration. Styles: free-standing, straw colored. and of irregular heights. Receptacle: light green, smooth, and in longitudinal section in the shape of a pitcher at the dehiscence of the anthers.

Development:

*Vegetation.*—Vigorous.

*Blooming.*—Abundant and fairly continuous.

*Aptitude to bear fruits.*—Very good.

*Resistance to frost.*—Good.

*Resistance to diseases.*—Very good.

I claim:

1. A new and distinct variety of Floribunda rose plant characterized by the following combination of characteristics:

(a) forms in abundance attractive long-lasting double blossoms which are a very stable aureolin yellow coloration,
(b) forms medium green adult wood,
(c) exhibits a compact and uniform low growth habit,
(d) exhibits very rapid reflowering cycles, and
(e) exhibits excellent resistance to diseases;

substantially as herein shown and described.

* * * * *

MEIBALTAZ